United States Patent [19]

Maus et al.

[11] Patent Number: 5,909,271
[45] Date of Patent: Jun. 1, 1999

[54] DEVICE FOR PERFORMING OPHTHALMIC PROCEDURES WITH IMPROVED ALIGNMENT

[75] Inventors: Roy C. Maus, North Bellmore; Anthony P. Cappo, New York; Gervey E. Mosquera, Bronx; Tomohiro Matsuzaki, Tuckahoe; Martin Gersten, New York, all of N.Y.

[73] Assignee: Computed Anatomy, Incorporated, New York, N.Y.

[21] Appl. No.: 08/957,633

[22] Filed: Oct. 24, 1997

[51] Int. Cl.$^6$ .......................................................... A61B 3/10
[52] U.S. Cl. ............................................ 351/212; 351/221
[58] Field of Search ..................................... 351/212, 221, 351/246, 247, 255, 250, 211, 208, 210

[56] References Cited

U.S. PATENT DOCUMENTS

| | | |
|---|---|---|
| 2,212,211 | 8/1940 | Pfund . |
| 3,181,351 | 5/1965 | Stauffer . |
| 3,598,478 | 8/1971 | Townsley . |
| 3,639,043 | 2/1972 | Townsley . |
| 3,797,921 | 3/1974 | Kilmer et al. . |
| 4,685,140 | 8/1987 | Mount, III . |
| 4,692,003 | 9/1987 | Adachi et al. . |
| 4,721,379 | 1/1988 | L'Esperance . |
| 4,772,115 | 9/1988 | Gersten et al. . |

(List continued on next page.)

FOREIGN PATENT DOCUMENTS

| | | |
|---|---|---|
| 1675827 | 4/1988 | U.S.S.R. . |
| WO 92/01417 | 2/1992 | WIPO . |

OTHER PUBLICATIONS

Greivenkamp, et al., "Measurement of Toric Reference Surfaces with the Computed Anatomy Videokeratoscope (TMS–1)" University of Arizona Optical Sciences Center and Department of Ophthalmology, 54/OFD2–1.

Shyh–shiaw Kuo "Image Recovery Using Row–Action Projection Methods" AT&T Bell Laboratories, pp. 109–132.

Mammone, et al., "3–D Corneal Modeling System" Biomedical Engineering, vol. 37, No. 1, Jan. 1990 pp. 65–72.

Mammone, et al., "High–numerical–aperture Reflecting Microscope" Department of Electrical and Computer Engineering, pp. 1–5.

Suganuma et al., "Three–dimensional shape analysis by use of a projected grating image" Optical Engineering Oct. 1991, vol. 30. No. 10. pp. 1529–1533.

Takeda et al., "Fourier transform profilometry for the automatic measurement of 3–D object shapes" Dec. 15, 1983, vol. 22. No. 24, Applied Optics. pp. 3977–3982.

Takeda, et al., "Fourier–transform method of fringe pattern analysis for computer–based topography and interferometry" Journal of Optical Society of America, vol. 72, No. 1, Jan. 1982, 155–160.

Tribolet, et al. "A New Phase Unwrapping Algorithm" IEEE Transactions on Acoustics, Speech, & Signal Processing, vol. ASSP–25, No. 2, Apr. 1977. pp. 169–177.

*Primary Examiner*—Hung Xuan Dang
*Attorney, Agent, or Firm*—Fish & Richardson P.C.

[57] ABSTRACT

An ophthalmic apparatus has instrumentation for performing an ophthalmic procedure on a patient's eye when the patient and the instrumentation are aligned with each other with respect to orthogonal X, Y, and Z axes. The Z axis specifies the distance of the eye from the instrumentation. A signal generator generates an initiation signal to initiate alignment of the instrumentation and the eye. An X-Y alignment apparatus and a Z alignment apparatus each respond to the initiation signal to cause alignment along their respective axes and then determine when the instrumentation and the eye are in predetermined relative positions along the Z axis. The X-Y alignment apparatus and the Z alignment apparatus each generate a respective alignment signal. A controller receives the Z alignment signal and the X-Y alignment signal and issues a control signal to the instrumentation to perform an ophthalmic procedure in response to the alignment signals.

37 Claims, 9 Drawing Sheets

U.S. PATENT DOCUMENTS

| | | |
|---|---|---|
| 4,794,550 | 12/1988 | Greivenkamp, Jr. . |
| 4,805,129 | 2/1989 | David . |
| 4,832,447 | 5/1989 | Javidi . |
| 4,863,260 | 9/1989 | Gersten et al. . |
| 4,964,715 | 10/1990 | Richards . |
| 4,974,094 | 11/1990 | Morito . |
| 4,978,213 | 12/1990 | El Hage . |
| 4,984,883 | 1/1991 | Winocur . |
| 4,995,716 | 2/1991 | Warnicki et al. . |
| 5,009,498 | 4/1991 | Gersten et al. . |
| 5,018,850 | 5/1991 | Gersten et al. . |
| 5,054,907 | 10/1991 | Sklar et al. . |
| 5,110,200 | 5/1992 | Snook . |
| 5,144,495 | 9/1992 | Merton et al. . |
| 5,193,124 | 3/1993 | Subbarao . |
| 5,214,456 | 5/1993 | Gersten . |
| 5,293,533 | 3/1994 | Klyce . |
| 5,300,965 | 4/1994 | Kitajima . |
| 5,357,294 | 10/1994 | Shimizu et al. . |
| 5,384,608 | 1/1995 | Gersten . |
| 5,412,441 | 5/1995 | Tibbling et al. . |
| 5,416,539 | 5/1995 | Gersten et al. . |
| 5,530,772 | 6/1996 | Storey . |
| 5,550,697 | 8/1996 | Green et al. . |

DEVICE FOR PERFORMING OPHTHALMIC PROCEDURES WITH IMPROVED ALIGNMENT

BACKGROUND OF THE INVENTION

The invention relates to an apparatus for performing ophthalmic procedures on a patient's eye.

One type of apparatus used to perform an ophthalmic procedure on a patient's eye is a keratoscope, which generates images of a patient's eye. In use of a keratoscope, the patient is positioned to look into the device, which must then be accurately positioned with respect to the patient's eye along a Z axis (which is defined as a line that essentially passes out of the center of the pupil into the device) and X and Y perpendicular axes (extending sideways and up and down with respect to the Z axis). A keratoscope projects illuminated concentric rings onto the cornea, and the appearance of the rings in an image of the eye along the Z axis is used in determining the topography of the patient's eye. Once determined, this information can be used for correctly fitting contact lenses to the patient, for corneal transplant surgery, disease detection, as well as several other medical uses.

SUMMARY OF THE INVENTION

The present invention features an ophthalmic apparatus which includes instrumentation for performing an ophthalmic procedure on a patient's eye when the eye and the instrumentation are aligned with each other with respect to orthogonal X, Y, and Z axes. The Z axis specifies the distance of the eye from the instrumentation. An initiation signal is generated to initiate alignment of the instrumentation and the eye. A Z alignment apparatus then responds to the initiation signal to cause alignment along the Z axis. The Z alignment apparatus determines when the instrumentation and the eye are in predetermined relative instrumentation and the eye are in predetermined relative positions along the Z axis and generates a Z alignment signal. The Z axis alignment apparatus can include a motor that moves the instrumentation along the Z axis with respect to the eye, and a Z position sensor that is carried by the instrumentation for movement with the instrumentation along the Z axis.

The ophthalmic apparatus includes an X, Y alignment apparatus which responds to the initiation signal to determine when the instrumentation and the eye are aligned along the X, Y axes and thereby generate an X, Y alignment signal. A controller then receives the Z alignment signal and the X, Y alignment signal and issues a control signal to the instrumentation to perform the ophthalmic procedure in response to the alignment signals.

In one embodiment, the X, Y axis alignment apparatus includes a light source that directs a positioning light beam to the eye and a detector that detects a reflection of the positioning light beam from the eye. The X, Y alignment apparatus can have a circuit that determines if electronic images from a camera include a reflection of the beam within a predetermined X, Y region on the eye.

In an alternative embodiment, the X,Y alignment apparatus features a fixation light beam for causing the patient to move the eye to align it in the X and Y axes. The light beam is directed along a positioning axis that passes through the center region of a pupil of the patient's eye when the apparatus is aligned with the patient's eye. Optics cause the light beam to converge in the region occupied by the patient's eye and to be imaged on the patient's retina. The light beam is sized so as to fill the majority of a standard pupil size associated with a level of illumination of the apparatus, whereby movement of the center region of the pupil away from the axis will cause the light beam to be eclipsed by the pupil. In this manner, a patient maintaining an uneclipsed view of the beam will be aligned with the axis.

The present invention also features a method of performing an ophthalmic procedure on a patient's eye. The method includes providing instrumentation for performing the procedure when the eye and the instrumentation are aligned with each other with respect to orthogonal X, Y, and Z axes. The method generates an initiation signal to initiate alignment of the instrumentation and the eye and then causes alignment along the Z axis by a Z alignment apparatus which responds to the initiation signal by determining when the instrumentation and the eye are in predetermined relative positions along the Z axis. A Z alignment signal is generated by the Z alignment apparatus. Alignment is then caused along the X, Y axes by an X, Y alignment apparatus responding to the initiation signal. The X, Y apparatus then generates an X, Y alignment signal. A control signal is issued to the ophthalmic instrumentation to perform the ophthalmic procedure in response to the alignment signals.

The present invention features an apparatus for positioning ophthalmic instrumentation with respect to a patient's eye along an axis. The apparatus includes a motor, a position sensor, and a controller. The motor is connected to move the ophthalmic instrumentation along the axis with respect to the eye. The position sensor is carried on the instrumentation and senses the position of the instrumentation with respect to the eye along the axis. The controller responds to the position sensor to issue a control signal to the apparatus at a predetermined position of the apparatus along the axis with respect to the eye.

In an alternative embodiment, the apparatus for positioning ophthalmic instrumentation has a control signal which stops the motor when the instrumentation is at the predetermined position. Alternatively, the control signal operates the instrumentation and can capture an image at the predetermined position.

The present invention also features an imaging apparatus that is movable with respect to a patient to capture an image of a portion of the patient, such as an eye, when the apparatus is at a predetermined position with respect to the patient. The imaging apparatus includes a camera that periodically outputs electronic images of the patient, a light source that is carried by the camera and directs a positioning light beam to the patient, and a controller that receives the electronic images and generates an image capture signal to capture the electronic image if the electronic image includes a reflection of the beam at the portion of the patient.

In an alternative embodiment, the controller of the imaging apparatus determines if the reflection of the beam is in a predetermined region within the electronic image. The controller receives the electronic image as serial pixel data and determines if the reflection is in the predetermined region before the pixel data for the entire electronic image has been received. The electronic image can include a frame comprised of two fields, and the controller then determines if the reflection is in the predetermined region in each field. Once the controller receives the electronic image to determine image intensity, a comparator then compares the intensity of pixel data at particular pixel positions with a threshold value characteristic of the reflection to determine if the reflection is in the predetermined position. The controller can include an occurrence monitor connected to the comparator to monitor occurrences of pixel intensity over the threshold. The controller can also include a line counter that counts lines of pixel data and a pixel counter that counts pixels within a line to enable the comparator to compare intensity values at particular pixel positions.

In an alternative embodiment, the imaging apparatus includes a position sensor carried on the instrumentation that senses the position of the instrumentation with respect to the eye along a Z axis. The controller responds to the position sensor to issue a control signal to the imaging apparatus at a predetermined position of the apparatus along the Z axis with respect to the eye. A motor can be connected to move the ophthalmic instrumentation along the Z axis with respect to the eye, and the control signal stops the motor when the instrumentation is at the predetermined position.

In an alternative embodiment, the control signal which is sent to the imaging apparatus generates the image capture signal upon meeting a Z axis condition and determining the existence of the reflection in a predetermined region within the electronic image. The captured image is an image analyzed for a pair of fields that comprise a single frame during the time that the two fields exist.

In an alternative embodiment, the camera includes an array of light sensing elements arranged in rows, and the position sensor includes a source of light that intersects the Z axis and a linear array of optical channels that receive light from the source. The number of channels receiving light are a function of the position of the instrumentation with respect to the portion of the body. The optical channels are linked to direct light to a row of sensing elements in the camera.

The present invention also features a patient-aligning ophthalmic apparatus which includes a light source to generate a light beam along a positioning axis that passes through the center region of a pupil of a patient's eye when the apparatus is aligned with the patient's eye. Optics cause the light beam to converge in the region to be occupied by a patient's eye and to be imaged on the patient's retina. The light beam is sized so as to fill the majority of a standard pupil size associated with a level of illumination of the apparatus, so that movement of the center region of the pupil away from the axis will cause the light beam to be eclipsed by the pupil. A target can be aligned with the axis to assist the patient. In this manner, a patient who maintains an uneclipsed view of the beam will be aligned with the axis.

In an alternative embodiment, the patient aligning ophthalmic apparatus includes a camera that periodically outputs electronic images of a portion of the patient's eye, including the pupil and the cornea. A controller receives the electronic images and generates an image capture signal to capture the electronic image if the electronic image includes a reflection of the beam in a predetermined region. The light beam is smaller than standard pupil size by an amount selected to maintain the reflection within the predetermined region when the image is not eclipsed by the pupil.

The present invention also provides an apparatus for determining the position of instrumentation with respect to a patient along an axis. The apparatus includes a light source, a linear array of light receiving elements, and a detector to detect light received at individual elements. The light source is carried by the instrumentation so as to direct a light beam to intersect the axis. The linear array of light receiving elements, such as optical fibers, are spaced along an optical path from the light source on an opposite side of the axis from the light source so as to provide a region for receiving a portion of the patient between the source and the elements. The number of elements blocked by the portion of the patient is a function of the position of the instrumentation with respect to the patient. The light receiving elements can be linked to an array of sensing elements which are also used to image a portion of the patient.

In another embodiment, the apparatus for determining positioning includes a motor to move the instrumentation along the axis and a controller that responds to the detector to stop the motor when the instrumentation is located at a desired position with respect to the patient.

DESCRIPTION OF THE PREFERRED EMBODIMENTS

Figure 1:
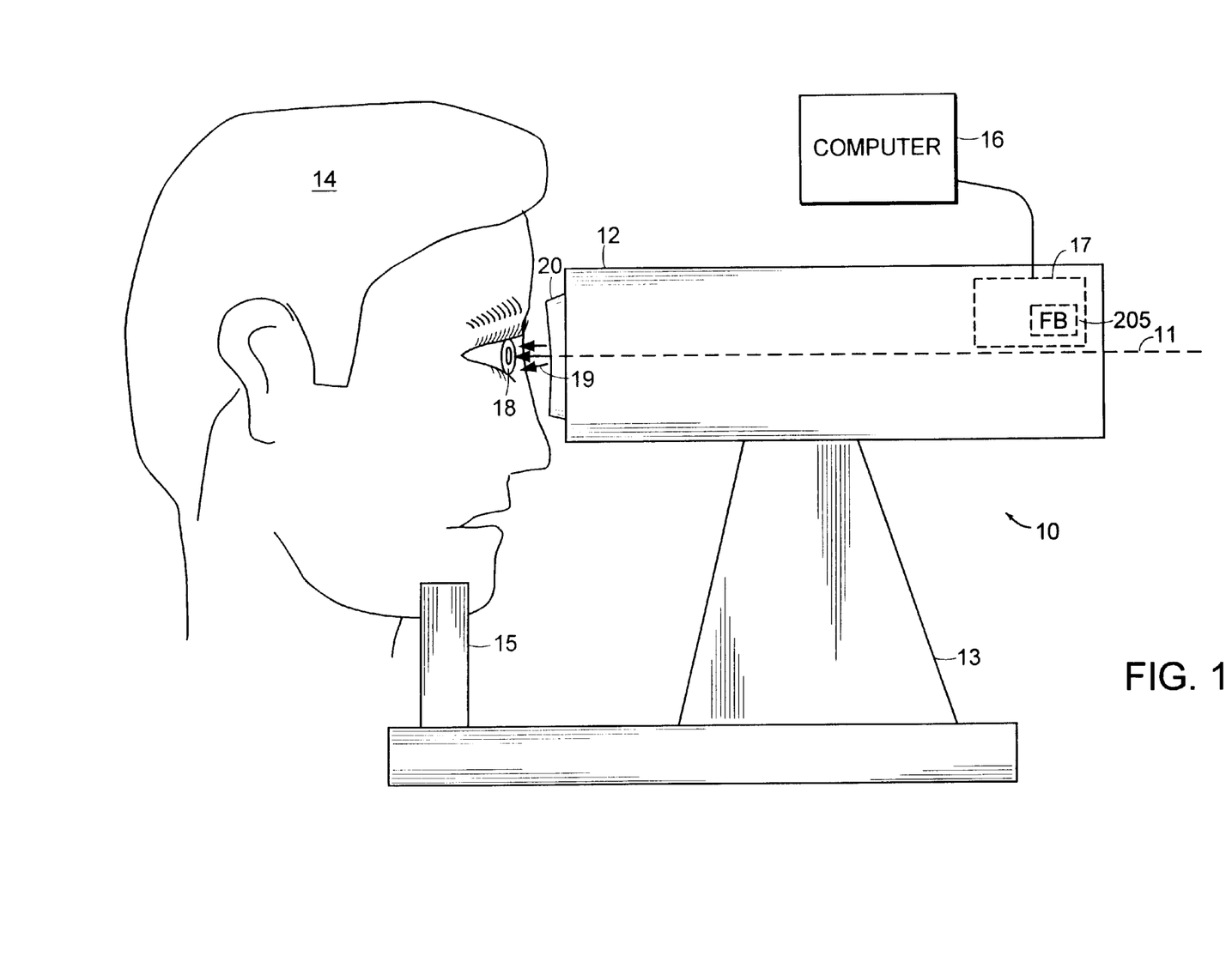
FIG. 1 is an illustration of an ophthalmic apparatus of the present invention in use by a patient.

Referring to FIG. 1, there is shown an automatically aligning keratoscope 10 in use by patient 14. The system 10 includes optical head 12, which is mounted on base 13 for automatic movement along Z axis 11 with respect to the eye 18 of patient 14. Chin rest 15 is used to fix the patient's head with respect to base 13. Optical head 12 projects concentric rings of light 19 onto the patient's eye, and includes optics and a camera (not shown on FIG. 1) for generating electronic images of the eye. Optical head 12 also includes internal circuit board 17 which carries circuitry that controls optical head 12, determines when optical head 12 is aligned with the patient's eye, and then captures an image of the eye and sends it to computer 16.

Figure 1A:
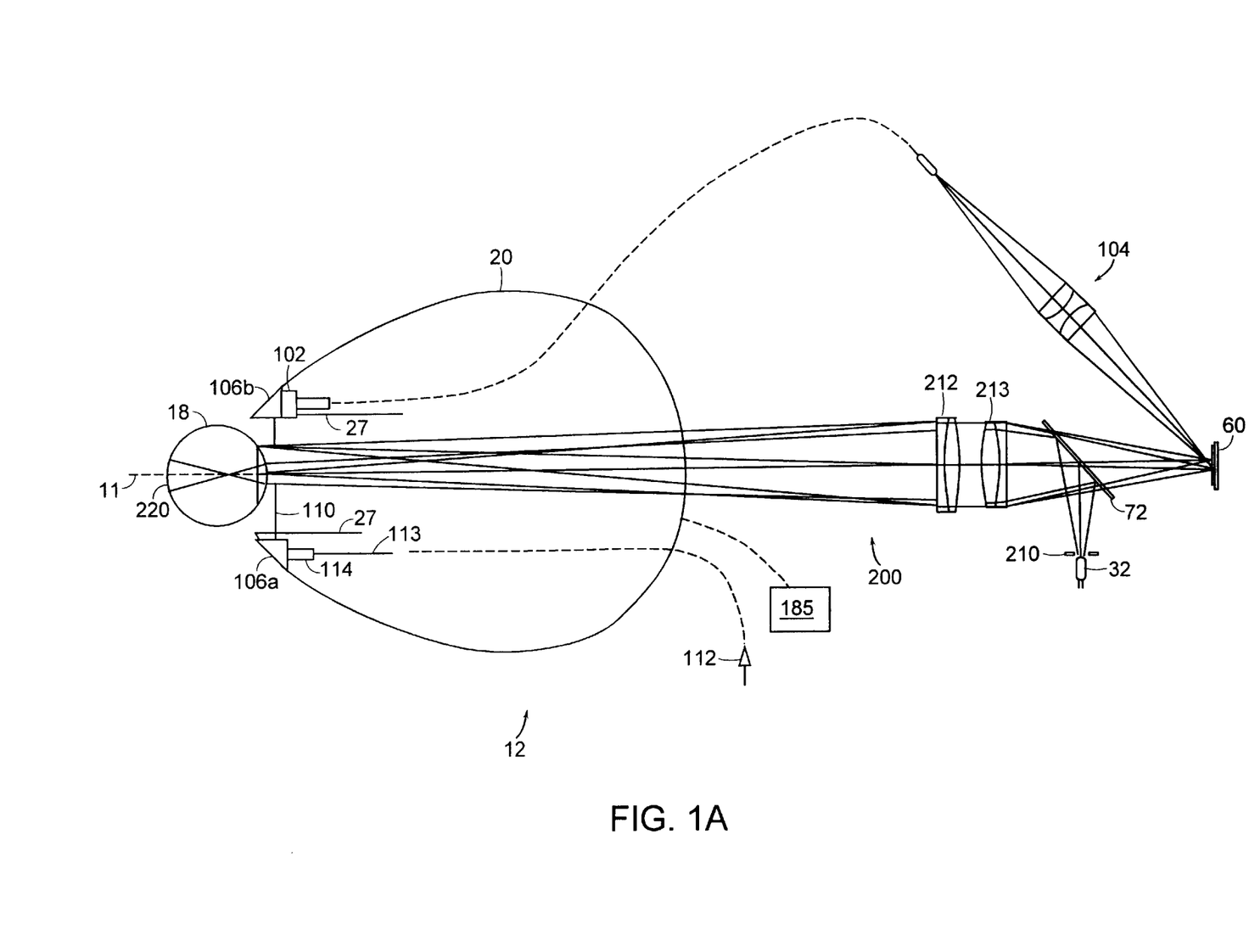
FIG. 1A is a diagram of components of an optical head of the FIG. 1 apparatus.

FIG. 1A shows the internal components of optical head 12. They include an egg-shaped enclosure 20 (which is positioned close to the patient's eye 18 and is used to project light rings on the eye and sense position along the Z axis), an X, Y alignment system 200 (which causes the patient to align eye 18 with respect to the X and Y axes), and charge coupled device (CCD) detector 60 (which is used to capture an image of the eye and also, in conjunction with circuitry 17, to determine when optical head 12 and eye 18 are properly aligned in the X, Y, and Z axes). The operations of the various components will be discussed in turn, before discussing the overall operation of the apparatus to automatically cause alignment with a patient and capture an image.

Pattern Illumination

Figure 2:
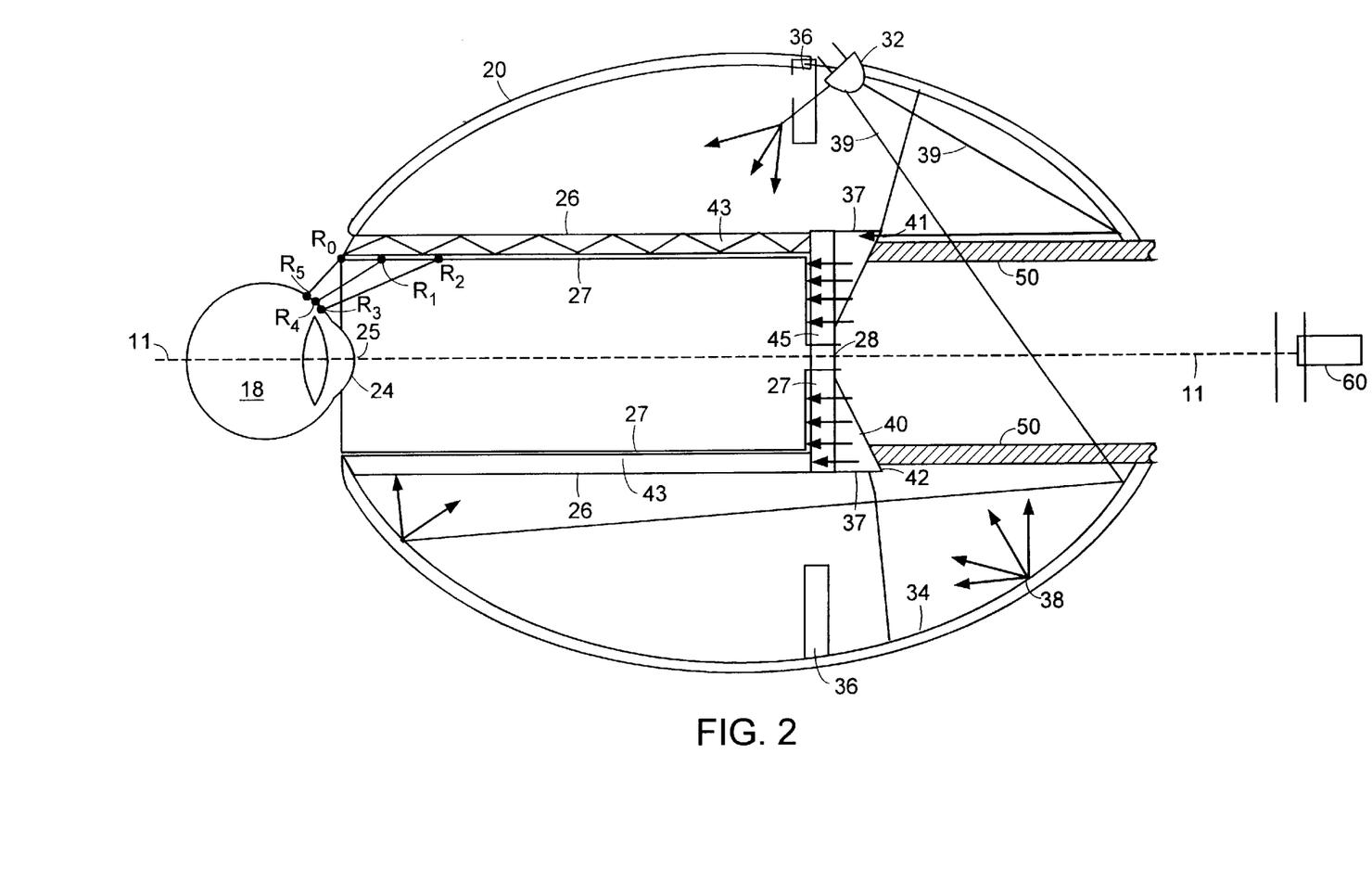
FIG. 2 is a diagrammatic vertical sectional view of pattern illuminating components of the FIG. 1 apparatus.

Referring to FIG. 2, the use of egg-shaped enclosure 20 to project concentric rings of light on the patient's eye will now be described. Enclosure 20 includes a transparent plastic cylinder 26 that carries a photographic film 27 on its internal surface that has opaque and transparent rings as described in U.S. Pat. No. 5,412,441. Light generated within enclosure 20 passes through transparent rings on cylinder 26 that are dimensioned to cause projection of concentric rings on the eye, as is known in the art and described in U.S. Pat. Nos. 4,772,115, 5,018,850 and 5,412,441. Corresponding rings on the film and projected rings on the eye are designated $R_0$, $R_1$, and $R_2$ in FIG. 2. The end of cylinder 26 is closed with transparent disk 45, which also has film 27 with opaque and transparent rings that are illuminated to provide the rings at the center portion of the ring pattern projected onto eye 18, as described in more detail below. Disk 45 also has opening 28 through which the patient's eye 18 is viewed by CCD detector 60. Tube 50 extends from the back of cylinder 26 to the rear surface of enclosure 20 and is used to mounting and aligning enclosure 20 with respect to optical components.

Enclosure 20 is made of two pieces of injection molded plastic (e.g., ABS) joined together at a vertical seam in the vicinity of eight LEDs 32 that are equally spaced around the periphery of enclosure 20 at the position shown for one LED on FIG. 2. LEDs advantageously are consistent in color, intensity and physical shape, are reliable and require low power. However, they have low power output and generate light of uneven intensity. The internal surface of enclosure 20 and the outer surface of tube 50 have light scattering properties so as to scatter light from the LEDs in order to uniformly and efficiently distribute the light before it passes through cylinder 26, thereby avoiding areas of high intensity in the rings projected on the eye. These surfaces have high light scattering properties with nearly zero absorption of the light and can, for example, be provided by a white powder-like substance, such as barium sulfate. Light 39 from LEDs 32 strikes the internal surface 34 of enclosure 20 and scatters in various directions with each bounce 38 off of the surface 34. Theoretically, each point on the surface 34 is illuminated with light from a light source 32 after several bounces. Light is, therefore, trapped and only exits enclosure 20 through cylinder 26, promoting the efficiency of use of the light generated by the LEDs 32.

LEDS 32 are directed toward the rear of enclosure 37 so that the light cannot pass directly through cylinder 26, but must first be scattered by the internal light scattering surfaces. LEDs typically have a component directed sideways at about 90°, and internal ring of white translucent plastic 36 (e.g., of Mylar) is used to diffuse this light and prevent it from passing directly to cylinder 26, to avoid areas of high intensity in the rings projected on the eye 18.

The majority of light used to generate rings passes through the wall of cylinder 26 within enclosure 20. In addition, light that hits surface 37 at the rear of cylinder 26 is reflected at angled surface 40 and passes through disk 45 to illuminate the ring pattern for the central rings carried on film on the front of the disk 45. Also, light that hits rear surface 41 (FIG. 2) outside of tube 50 is transmitted by total internal reflection (indicated at 43 on FIGS. 2 and 3) within the sidewall of the cylinder 26 to an angled surface at end portion 47 (FIG. 3) of cylinder 26, where the light is reflected to illuminate rings on cylinder 26 outside of enclosure 20. Rings are placed at end portion 47 extending from enclosure 20 to create a space for the patient's face. Enclosure 20 is elliptical (varying from an ideal spherical shape for the light scattering surface) with a smaller dimension near the front to also accommodate a patient's face.

A combination of different wavelengths of light can be used for the LEDs to produce a variety of effects.

Z Axis Position Sensing

Figure 3:
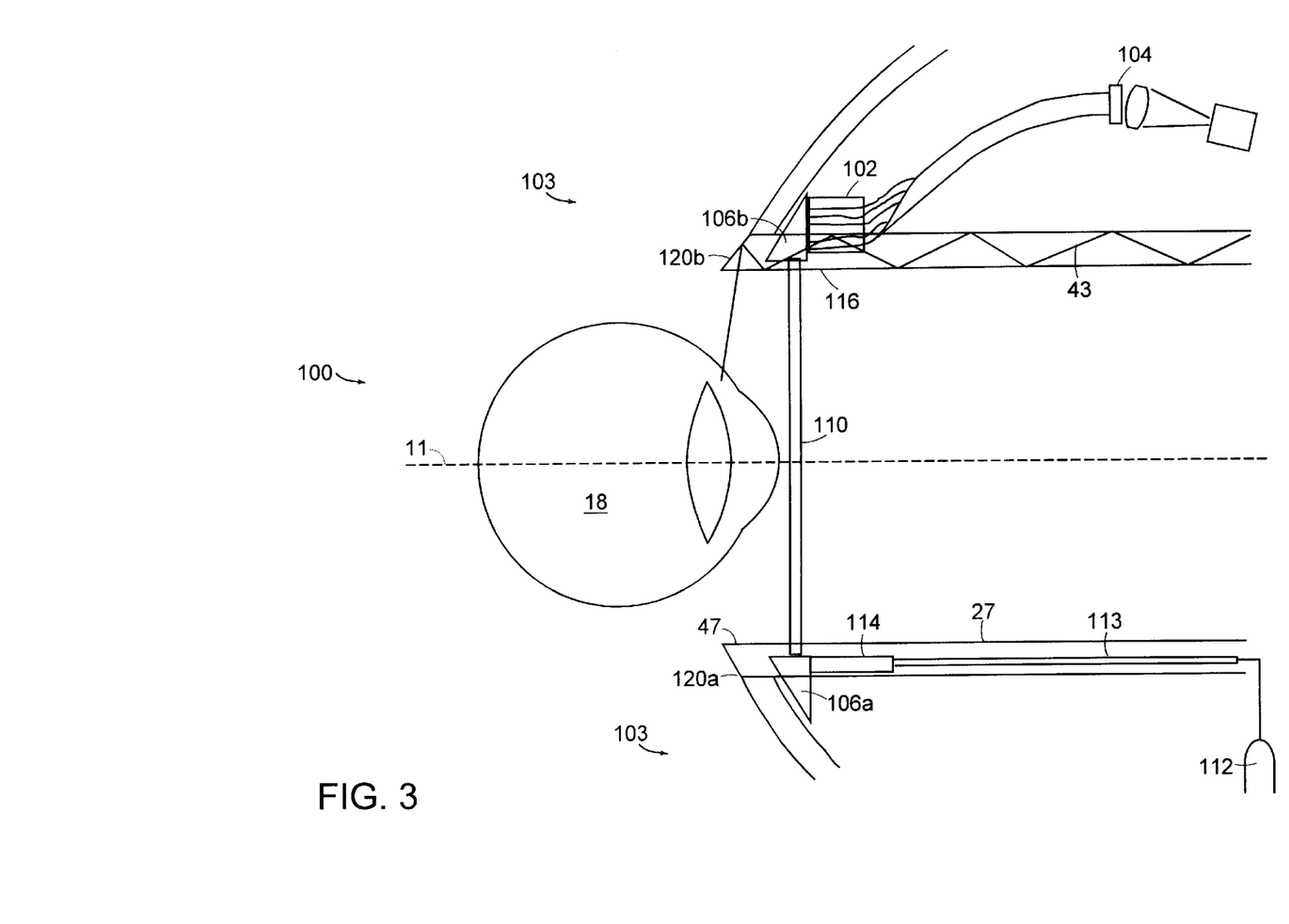
FIG. 3 is an enlarged view of an end of an enclosure of the FIG. 2 pattern illuminating components.

Referring now to FIGS. 1A and 3, the components used to sense the position of optical head 12 with respect to eye 18 along Z axis 11 will now be described. Light from emitter 112 (carried on circuit board 17 shown in FIG. 1) is transmitted through 1 mm optical fiber 113 which terminates at a gradient index lens 114. Lens 114 is mounted on a prism 106, which redirects the light and projects a 1 mm light beam 110 perpendicular to Z axis 11 at the front of optical head 12. Light beam 110 is received on the opposite side of Z axis 11 by a second prism 106$b$, which redirects the light 90° to linear fiber optic array 102. Light from the other end of fiber optic array 102 is directed through an imaging lens 104 to specific horizontal lines (in particular the fifth lines of each of the odd and even fields, as discussed below) of sensing elements of CCD detector 60. Linear fiber optic array 102 extends preferably 3 mm and includes 70 micron fibers. Beam 110 is preferably 1 mm wide and is directed to a central portion of the 3 mm linear array of 70 micron fibers. As the eye and optical head are moved closer to each other along Z axis 11, portions of the beam directed to fibers at one end of the array begin to be blocked, and the linear array of fibers thus acts as a ruler measuring the position of the eye along the Z axis. Prisms 106$a$ and 106$b$ are optically aligned with each other by "windows" in the film 27 of the ring pattern for the emitter 112 and receiver 116 to "look" through. This employs the inherent accuracy and repeatability of the photographic method used to create the ring pattern in aligning prisms 106$a$, 106$b$.

Mounting LED emitter 112 on circuit board 17 and delivering light to the area to be sensed by fiber optic cable 113 and prism 106$a$ conserves space at the end of the optical head near the patient and keeps the emitter away from the patient. On the receiving end, fibers 102 and prism 106$b$ deliver the sensed light signals of interest to the CCD detector 60, similarly conserving space at the region of interest near the patient. The other end of this array 102 is imaged directly on to the CCD detector 60 used for image acquisition in a region of the CCD 60 not used for the ring pattern image. Optical head 12 can thus analyze the image data to determine if there is proper alignment in the Z axis. Using the CCD 60 to sense Z position eliminates the need for an additional sensor and provides an actual image of the Z position in the image of the eye captured and transferred to the device's computer 16.

The beam of IR light 110 across the cylinder 26 is placed such that the central portion of the beam 110 is focused on a predetermined region of the fiber optic linear array 102 on the opposite side of the cylinder 26. The midpoint of this region is placed such that it is in the middle of the Z axis range which is determined to be the point of calibration of the device 12 where it is acceptable to acquire an image of the patient.

X, Y Alignment

Figure 4A:
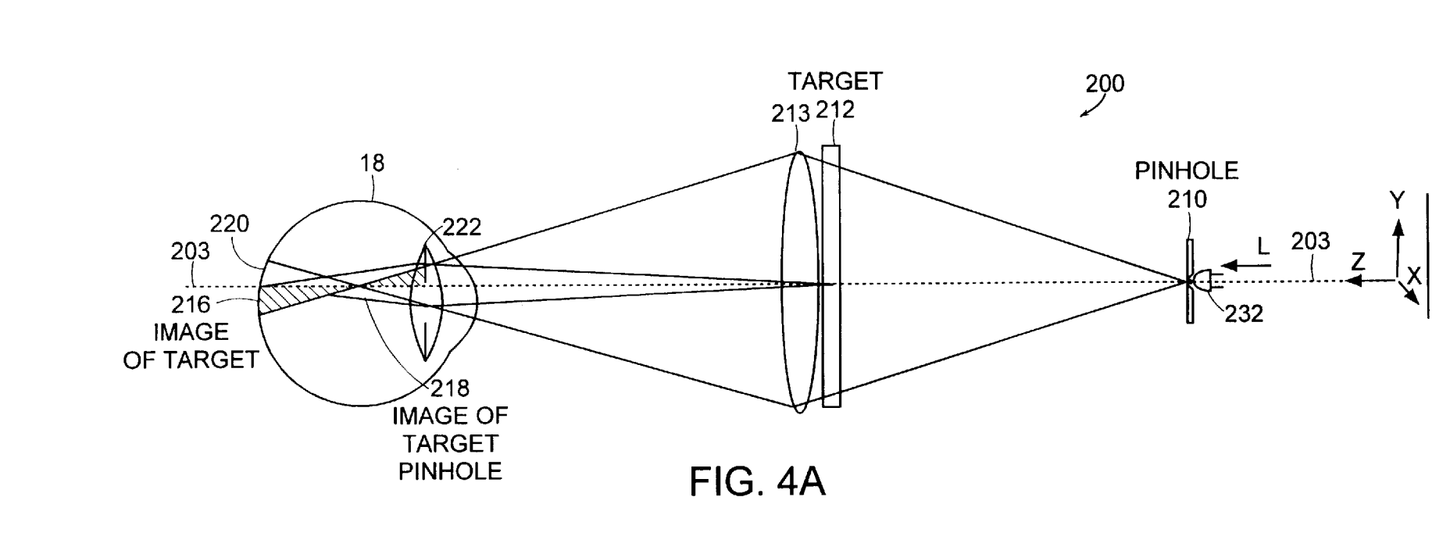
FIG. 4A is a diagram showing the fixation and alignment system of the FIG. 1 apparatus.

Referring now to FIGS. 1A and 4A–E, the components of optical alignment system 200 used to cause the patient to self-align eye 18 in the X and Y axes will now be described. Referring to FIG. 1A, optical alignment system 200 includes a point light source 32 projecting light through a target 210 which can be received by a beam splitter 72. The light travels through lenses 213 along Z axis 11 and projects onto the patient's eye 18. The optical alignment system 200 also includes a target 212. The optical diagram shown on FIG. 4A does not include beam splitter 72, but shows the converging nature of the fixation beam employed and its relationship with the pupil. Referring to FIG. 4A, the light is focused by lens 213 to produce a convergent beam at the cornea of the eye 214. The eye focuses the beam at 222 to produce an image of the target pinhole 218 somewhere between the lens 222 and the retina 220 of the eye 18, the location depending upon an individual person's vision. This produces a defocused image of the target 216 on the retina 220. This appears to the patient as a large patch of light since the lens aperture is actually being imaged onto the retina 220.

The size of the target image 216 formed on the retina 220 is determined by the size of the pin hole 210 used in the system 200. The pin hole size is determined by an average of the patient pupil diameter for any given illumination system. In the closed optical system of the present invention in which the illumination characteristics are controlled, it is determined that the average pupil size is approximately 3 mm. For any given closed system, however, the desired pupil size can be determined through testing and the pin hole size can be adjusted for that system.

Figure 4B:
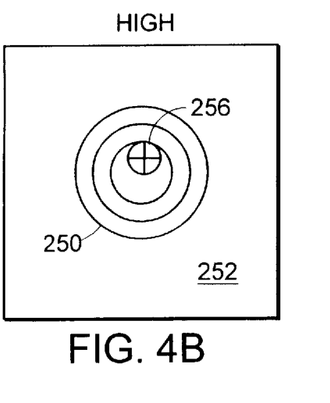
FIGS. 4B–4E illustrate what is seen by a patient during self-alignment with a positioning axis of the FIG. 1 apparatus.
Figure 4C:
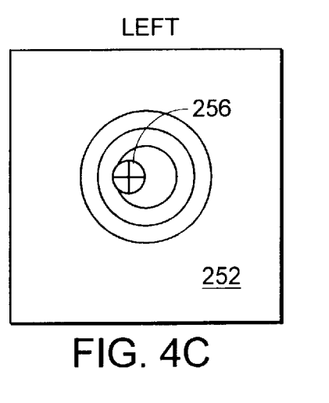
Figure 4D:
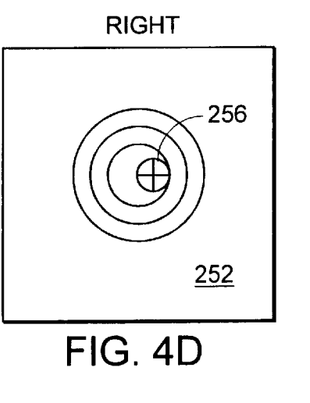
Figure 4E:
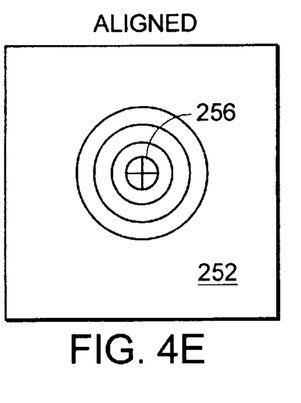

FIGS. 4B–4E illustrate what is seen by a patient looking into optical head 12. The patient sees ring pattern 250 (generated by the rings on disk 45) and bright patch of light 252 generated by source 32 and pin hole 210. These figures illustrate the effect of the patient's eye movement on patch of light 252. If the patient's pupil moves off axis 11 slightly, the edge of the pupil begins to cut into the beam and thereby causes a shadow 256 on the patch of light 252 which falls onto the retina 220. The shadow 256 moves in the same direction as the patient's movement. For instance, if the patient moves down, the top of the patch of light 252 begins to shadow. This shadow 256 increases as the patient continues to move his or her pupil in a given direction until the pin hole image 218 finally disappears by being totally blocked by the edge of the iris. As shown in the illustrations, this shadow occurs in any direction that the patient moves. FIGS. 4B–4D illustrate patient movement which is above, to the left, and to the right of axis 11. FIG. 4E illustrates a pupil which is aligned with axis 11.

In order to assist the patient in keeping the eye 214 properly aligned with axis 11, target 212 is added to the system 200 to provide the patient with a fixation point. The target 212 is preferably placed at the surface of the lens 213, or within the focal length of the lens 213 which is in focus on the retina 220. The target 212 can not be placed at the pin hole 210 since this is out of focus with the retina 220. The target 212 remains stationary as the patient moves, and patch of light 252 behaves as if there was no target present. In essence, the target 212 acts as a cue for the patient. The patient attempts to keep the target, such as a cross pattern, in the middle of the bulls eye formed by the rings 250. This allows patients with various vision abilities to successfully fixate on an object on the system and therefore align with the light axis. Further, this targeting method operates over a visual acuity range of +16 to −16. Patients who are myopic focus on target 212, which is near to the eye 214, whereas patients who are hyperopic focus on pinhole 210 which represents a much further distance.

From the detector's 60 point of view, the image of the fixation light in the eye 214 shows no evidence of the target 212 or a large patch of light 252. The image formed in the cornea is of similar size as ophthalmic systems which use a collimated fixation beam. This occurs because the light beam is preferably only slightly convergent, and therefore, similar to collimation beams, so that it produces an image size nearly identical to collimated systems. The target 212 is not imaged anywhere in the overall system except the patient's retina 220.

The fixation beam 203 is reflected off of the front of the patient's cornea and appears as a point of high intensity in the image viewed by CCD 60. This point appears within a central region of the image when the eye is properly aligned in the X and Y axes. Optical head 12 can thus analyze the image data to determine if there is proper alignment in the X and Y axes.

Optical Head Circuitry

Figure 8:
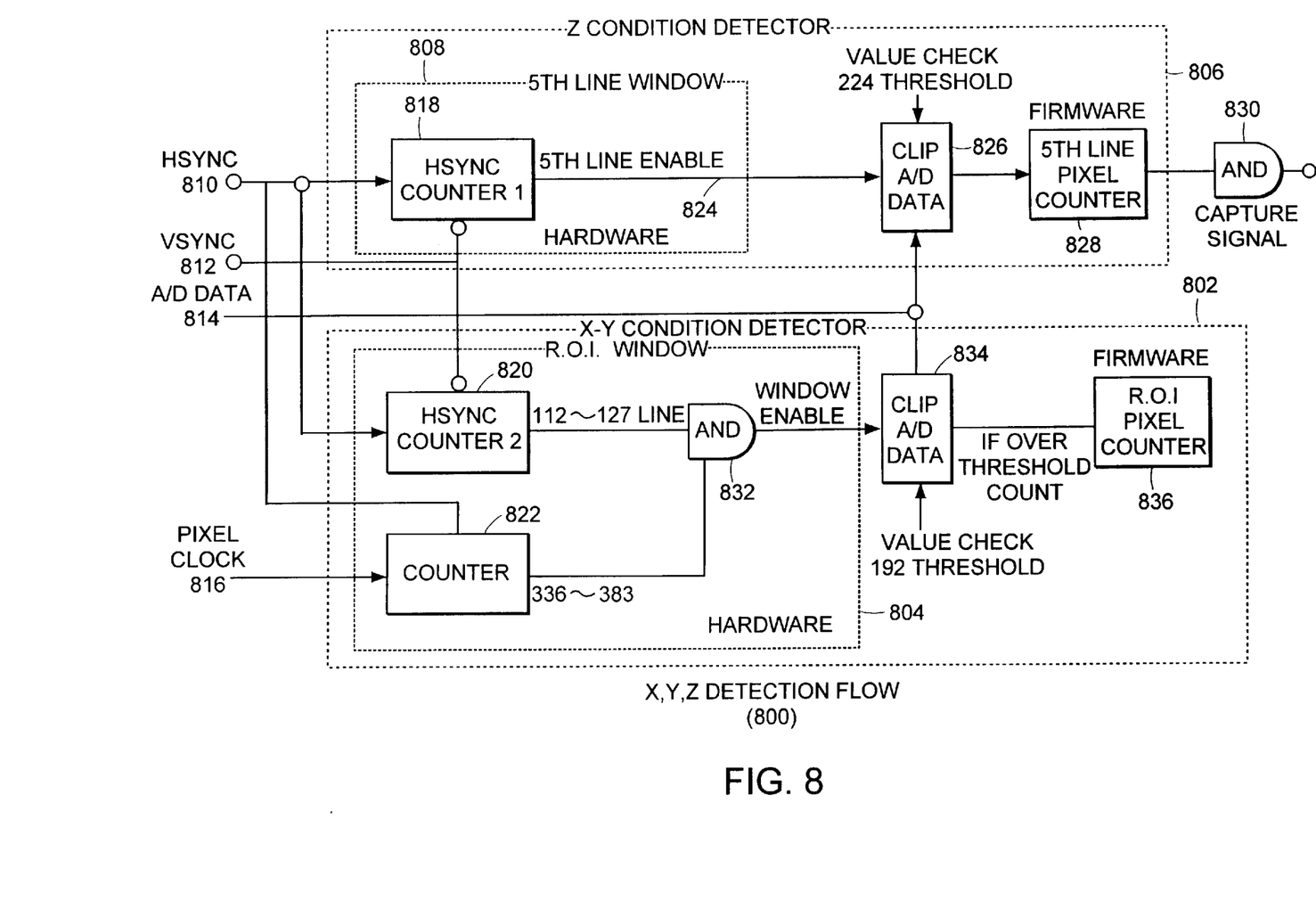
FIG. 8 is a detection flow diagram with the X, Y, and Z axes conditions.

FIG. 8 shows the X,Y,Z detection circuitry 800 used to analyze pixel data received from CCD detector 60 to determine when the Z condition and X, Y conditions have been met. CCD detector 60 generates images of the eye at the rate of 30 frames per second. The images from CCD detector 60 also include a small number of horizontal lines with light projected from optic array 102 that indicates Z position. The images also include a reflection of the fixation beam off the front of the cornea used to determine X, Y alignment.

The pixel data are sent serially to circuit board 17, digitized at board 17, and stored in frame buffer 205 (FIG. 1). As each new frame is provided by CCD detector 60, it replaces the previous frame in the frame buffer. CCD detector 60 sends the images in fields of odd and even lines, one line at a time. The digitized data are provided as 8 parallel bits over bus 814. The detection flow circuitry 800 also receives Hsync signal 810, indicating a new horizontal line of pixel data, Vsync signal 812, indicating a new field, and pixel clock 816. Line counter 818 counts Hsync pulses and outputs an enable at the fifth line so that comparator 826 compares the intensity value (0–255) for all pixels in the fifth line of the odd and even fields with a threshold value of 224. Counter 828 counts the occurrences of values in the fifth line over the threshold. Line counter 820 counts Hsync pulses and outputs an enable from line 112 until line 127 to AND gate 832. Pixel counter 822 counts pixel clock pulses and outputs an enable to AND gate 832 from pixel 336 until pixel 383 in each horizontal line. The output of gate 832 enables comparator 834 to compare the intensity values for pixels 336–383 in lines 112–127 with a threshold value of 192. Counter 836 counts the occurrences of values in the fifth line over the threshold. Line counters 818 and 822 are cleared by Vsync pulse 812, and pixel counter 822 is cleared by Hsync pulse 810.

System Operation

After the power is turned on for the system, the host computer 16 sends a command to optical head 12, signaling that the system is ready to accept a picture. The patient 14 places his face on chin rest 15, and the device senses the patient's position via an IR proximity sensor (not shown), which preferably sees the patient's face when it is approximately 20 mm from optical head 12. Ring illumination LEDs 32, fixation light 232, and emitter 112 are turned on. After a short delay of preferably 1 second, the Z axis motor 185 begins moving the optical head 12 relative to base 13 toward the patient. The patient attempts to keep the cross target 212 in the approximate center of the bulls eye formed by the rings.

While optical head 12 is moving toward the patient and the patient is automatically moving the eye to maintain the position of the target relative to the pattern in the X,Y position, CCD detector 60 is generating images of the eye at the rate of 30 frames per second and transferring the image to a frame buffer. The images also include a small number of horizontal lines with light projected from optic array 102 that indicates Z position, and a reflection off the front of the cornea of the fixation beam 203. As the image data are transferred to a frame buffer 205, they are also analyzed to sense X, Y and Z position, as is described in more detail below with reference to FIGS. 5–8. Once the Z position is found, the Z axis motor 185 is instructed to stop. The control system checks the framebuffer condition for X, Y region of interest condition in the first field of the video signal. Once the X and Y condition are met in the first field of the video signal, the device rechecks the X, Y, and Z conditions in the second video frame. When the conditions are met, the device ceases digitizing the analog signal from CCD detector 60, and frame buffer control is instructed to freeze and transfer the analyzed frame to the host computer 16. The device lights are then turned off, and the Z axis motor 185 returns the optical head section to the initial position. The device then awaits for the host computer to resend a command to restart the cycle.

Figure 5:
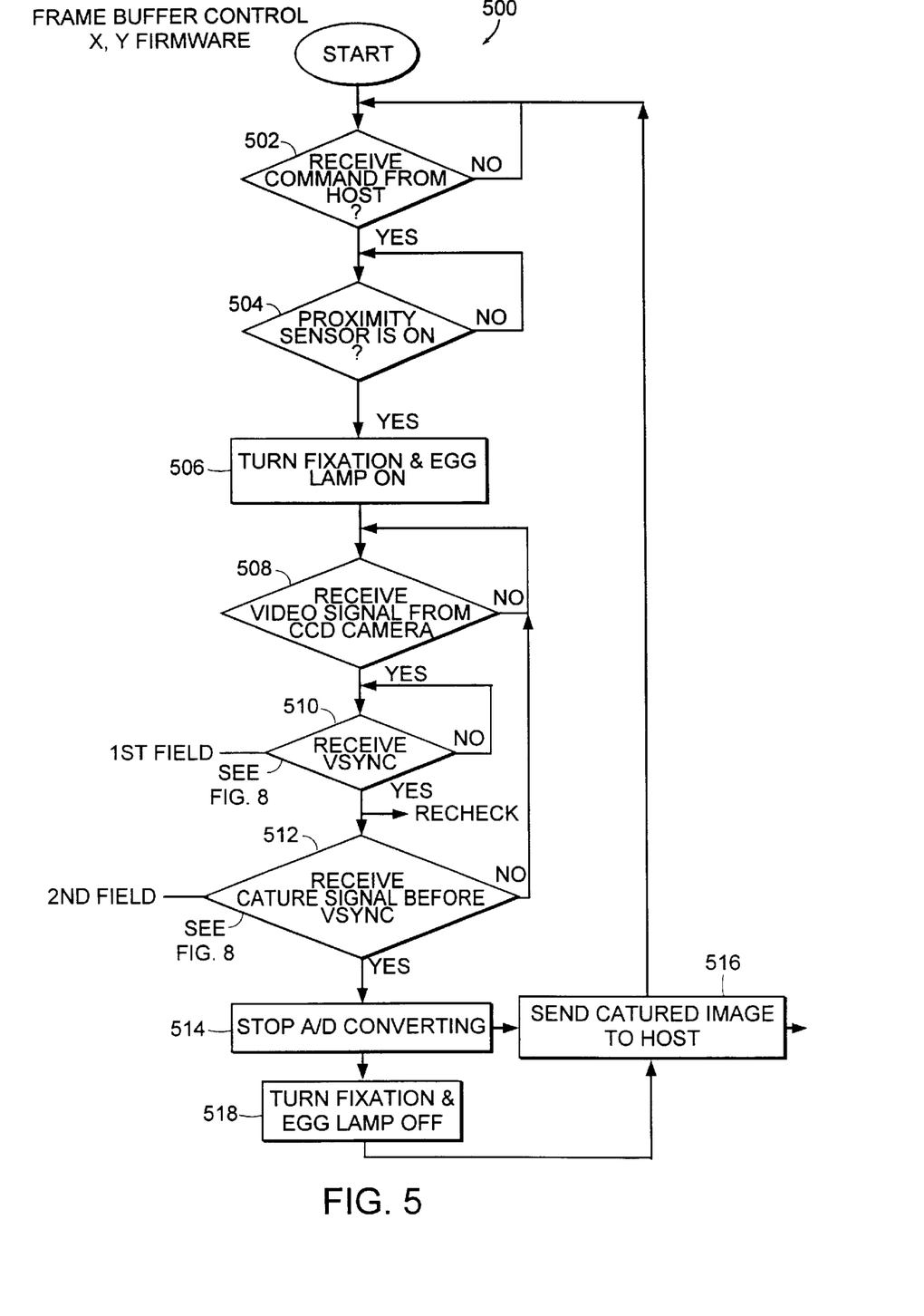
FIG. 5 is a flow diagram for the X-Y frame buffer control system.

Referring to FIG. 5, there is shown the frame buffer control system for the X, Y firmware 500. The command signal is first received from the host computer (Step 502), and once the signals are received the proximity sensor is turned on (Step 504). Next, the fixation light 232 and LEDs 32 are turned on (Step 506). The video signal is received from the CCD camera (Step 508) and analyzed for X, Y conditions as described in more detail below in connection with FIGS. 7 and 8. The end of the first field of the video frame is identified by the Vsync signal, and stored while the second field of video frame is received (Steps 510 and 512); if a "capture signal" (indicating X, Y, Z alignment) is not received before the Vsync indicating the end of the second field, the device returns to step 508 and receives the next frame. Once the captured signal is received, the analog/digital converting process is terminated (Step 514), and the captured image is sent to the host computer (Step 516). The lights of the device are then turned off (Step 518), thereby allowing this device to start the cycle again.

Figure 6:
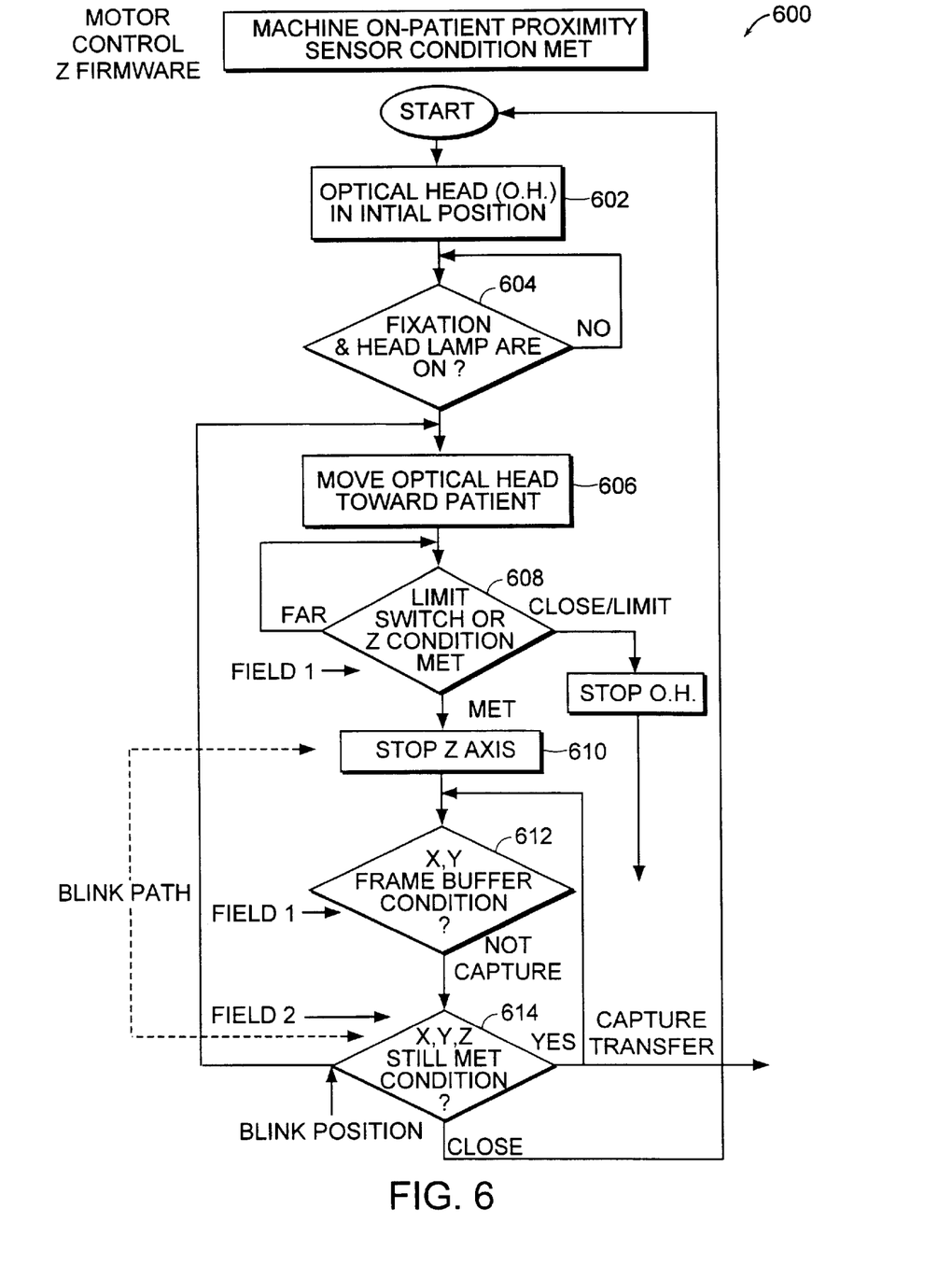
FIG. 6 is a flow diagram for the Z axis control system.

Referring to FIG. 6, there is shown the Z motor control algorithm 600. Once the machine has been turned on, and the patient proximity sensor conditions have been met, the optical head 12 begins the cycle at its initial position (Step 602). After the fixation and LEDs are turned on (Step 604), the optical head section moves towards the patient (Step 606). The movement on the optical head section is terminated when the limit switch (indicating that the optical head has come too close to the patient's face) or the Z condition is met (Step 608). Once the Z condition is met, the Z axis motor 185 stops its movement (Step 610). The motor control system 600 then checks the X-Y framebuffer control system of FIG. 5 (Step 612) to determine the status of the video fields. In (Step 614) a condition is tested to protect against an undesired image being tested, such as a patient blinking. If the test reads that the patient has blinked or that the light is from an image other than the surface which is to be examined, the system automatically readjusts by going back to Step 606. Once the X, Y, Z condition is met, the transfer is captured and the cycle is restarted.

The Z condition and X, Y conditions will now be described in detail. As the patient keeps the pupil of the eye 18 aligned with the middle of the ring pattern, the optical head 103 is moving toward the patient along the Z-axis. As the instrument starts to approach the proper Z position to take the image, the apex of the patient's cornea begins to eclipse, or block the IR signal 110 reaching the receiver 116 (FIG. 3) and imaged on the fifth lines of the odd and even fields of detector elements of CCD detector 60. In the 8-bit digitized intensity values for each pixel, 0 represents black and 255 represents bright white. As the eye blocks the paths of light to optical fibers, pixel intensity values in the line in the detector will go from a high value to a low value. The Z position range is defined for the firmware and hardware as 4 of the receiving fibers on either side of the calibration position. That is, the device 12 will accept an image that is at the zero position, the calibration point or 280 microns before or after that position. A threshold value of 224 is used at comparator 826 to identify when a fiber was or was not blocked by the patient's eye, because no other video signal in the region of interest exceeds this value and therefore any signal above this level represents an unblocked fiber in the fiber optic array. Additionally, it is also known which fibers in the array (and thus what pixels in line 5) are in the acceptable Z position range, as defined at the time of the calibration of the instrument. This information is used to tell the firmware which pixels above the threshold should be counted to find the proper Z position. This analysis is performed during the digitization of the first field of the video. Since it has been chosen to use the fifth line counted in a video field, it becomes irrelevant which field the system initially chooses to look for the Z conditions. The first field which meets Z position criteria is termed as the "first" field. When this condition is met in the first field, the firmware instructs the Z axis motor to stop.

Figure 7:
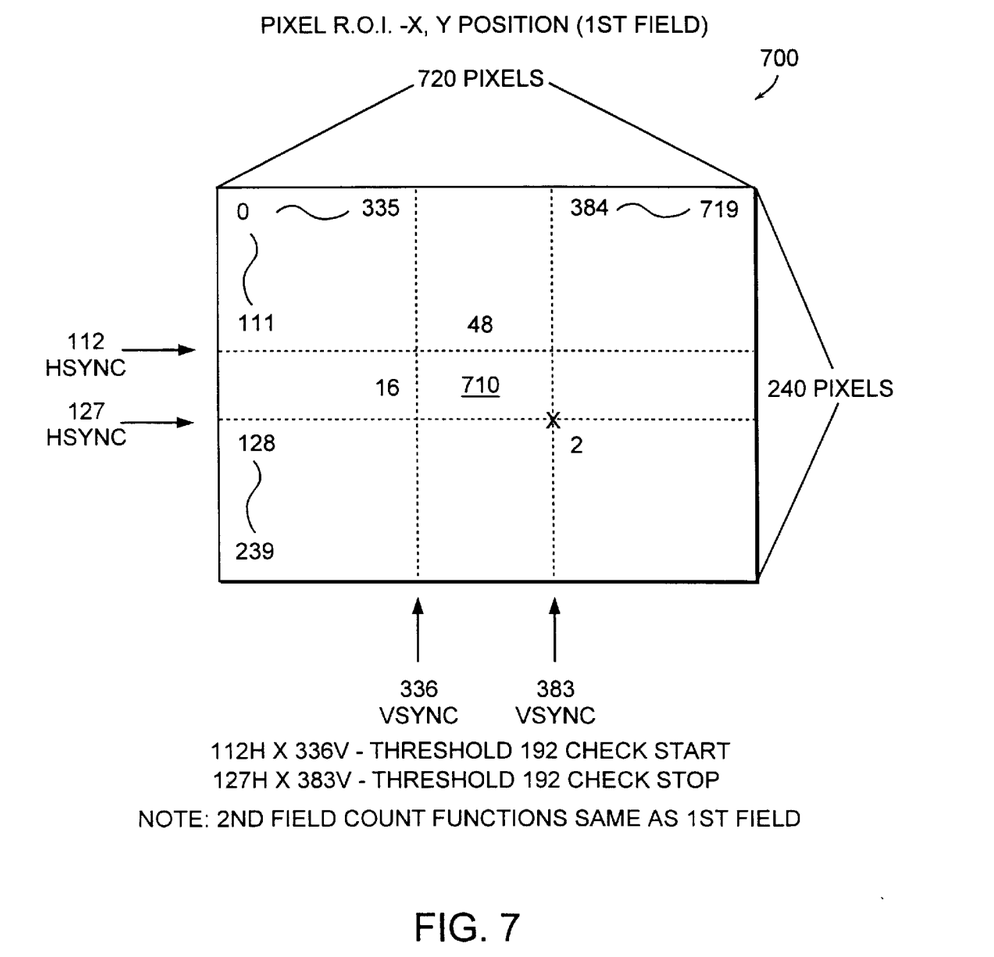
FIG. 7 illustrates a pixel region of interest used for X, Y alignment.

Referring now to FIG. 7, there is shown the pixel region of interest in field 700 of video pixels. Although only the first field is illustrated in FIG. 7, the same region of interest and procedure are employed in the second field. After determining that the Z position condition has been met, the X and Y region of interest is examined in a similar manner to the Z position within the first field of the video. The region of interest of the X,Y position is defined as the rectangle 710 in the middle of the digitized video in the buffer with the borders of horizontal line number 112 and horizontal line number 127. Vertical borders of the rectangle 710 start at pixel number 336 along the horizontal lines and end at pixel number 383 along the horizontal lines. The threshold intensity employed by comparator 834 is set at 192, and the firmware looks for greater than 3 pixels but less than 16 above the threshold. This range was determined because the reflection of the fixation light signal always has at least three but no more than 16 pixels over 192. Thus, if more than 16 pixels are present above this level, it is a signal from another light source, such as an image off of a patient's blink. The pixel counter firmware checks that the X, Y, Z conditions are met in the first field and then repeats the check in the second field of video.

Other embodiments of the invention are within the scope of the following claims. E.g., this method of analyzing the video in real time is extremely flexible and can be used to define any desired conditions for capturing an image and for controlling other devices, such as motion controls, lighting conditions, etc. The method of illumination is not specific to corneal topography devices and could be utilized with any device requiring even illumination of a surface. Additionally, different colors of light, and different numbers of light sources can be used depending upon the specific type of application intended.

This system of patient alignment is applicable to any ophthalmic instrument which it is desirable to have a patient align themselves.

The shape of enclosure 20 can be different than the egg-shape described so long as it has gently curving surfaces. E.g., the rear portion could more closely approximate a sphere.

What is claimed is:

1. An ophthalmic apparatus comprising, instrumentation for performing an ophthalmic procedure on a patient's eye when said eye and said instrumentation are aligned with each other with respect to orthogonal X, Y, and Z axes, said Z axis specifying the distance of said eye from said instrumentation, a signal generator that generates an initiation signal to initiate alignment of said instrumentation and said eye, Z alignment apparatus responsive to said initiation signal to cause alignment along said Z axis, said Z alignment apparatus determining when said instrumentation and said eye are in predetermined relative positions along said Z axis and generating a Z alignment signal, X, Y alignment apparatus responsive to said initiation signal to cause alignment along said X, Y axes, said X, Y alignment apparatus determining when said instrumentation and said eye are aligned along said X, Y axes and generating an X, Y alignment signal, and a controller that receives said Z alignment signal and said X, Y alignment signal and issues a control signal to said instrumentation to perform said ophthalmic procedure in response to said alignment signals.

2. The apparatus of claim 1 wherein said Z axis alignment apparatus includes a motor that moves said instrumentation along said Z axis with respect to said eye and a Z position sensor that is carried by said instrumentation for movement with said instrumentation along said Z axis.

3. The apparatus of claim 1 wherein said X, Y axis alignment apparatus includes a light source that directs a positioning light beam to said eye and a detector that detects a reflection of said positioning light beam from said eye.

4. The apparatus of claim 3 wherein said detector includes a camera that outputs electronic images, and said X, Y alignment apparatus includes a circuit that determines if said electronic image includes a reflection of said beam within a predetermined X, Y region on said eye.

5. The apparatus of claim 1 wherein said X,Y alignment apparatus provides a fixation light beam for causing said patient to move said eye to align it in said X and Y axes.

6. The apparatus of claim 5 wherein said light beam is directed along a positioning axis that passes through the center region of a pupil of said patient's eye when said apparatus is aligned with said patient's eye, and further comprising, optics causing said light beam to converge in the region to be occupied by a patient's eye and to be imaged on said patient's retina, said light beam being sized so as to fill the majority of a standard pupil size associated with a level of illumination of said apparatus, whereby movement of the center region of the pupil away from said axis will cause said light beam to be eclipsed by said pupil, such that a patient maintaining an uneclipsed view of said beam will be aligned with said axis.

7. The apparatus of claim 6 wherein said light beam is smaller than said standard pupil size by an amount equal to the permitted misalignment of said apparatus.

8. The apparatus of claim 1 wherein said signal generator is a proximity sensor.

9. The apparatus of claim 1 wherein said signal generator is a control button.

10. A method of performing an ophthalmic procedure on a patient's eye comprising, providing instrumentation for performing an ophthalmic procedure on a patient's eye when said eye and said instrumentation are aligned with each other with respect to orthogonal X, Y, and Z axes, said Z axis specifying the distance of said eye from said instrumentation, generating an initiation signal to initiate alignment of said instrumentation and said eye, causing alignment along said Z axis by Z alignment apparatus responsive to said initiation signal by determining when said instrumentation and said eye are in predetermined relative positions along said Z axis by said Z alignment apparatus, generating a Z alignment signal by said Z alignment apparatus, causing alignment along said X, Y axes by X, Y alignment apparatus responsive to said initiation signal, generating an X, Y alignment signal by said X, Y alignment apparatus, and issuing a control signal to said ophthalmic instrumentation to perform said ophthalmic procedure in response to said alignment signals.

11. An apparatus for positioning ophthalmic instrumentation with respect to a patient's eye along an axis comprising, a motor connected to move said ophthalmic instrumentation along said axis with respect to said eye, a position sensor carried on said instrumentation that senses the position of said instrumentation with respect to said eye along said axis, and a controller that is responsive to said position sensor to issue a control signal to said apparatus at a predetermined position of said apparatus along said axis with respect to said eye.

12. The apparatus of claim 11 wherein said control signal is a stop motor signal to stop said motor when said instrumentation is at said predetermined position.

13. The apparatus of claim 11 wherein said control signal is a signal to operate said instrumentation at said predetermined position.

14. The apparatus of claim 11 wherein said instrumentation includes a camera, and wherein said control signal is a signal to operate said instrumentation to capture an image at said predetermined position.

15. An imaging apparatus that is movable with respect to a patient to capture an image of a portion of a patient when said apparatus is at a predetermined position with respect to said patient comprising, a camera that periodically outputs electronic images of said portion, a light source that is carried by said camera and directs a positioning light beam to said portion of said patient, and a controller that receives said electronic images and generates an image capture signal to capture a said electronic image if said electronic image includes a reflection of said beam at said portion of said patient.

16. The apparatus of claim 15 wherein said portion is a portion of an eye of said patient.

17. The apparatus of claim 15 wherein said controller determines if said reflection is in a predetermined region within said electronic image.

18. The apparatus of claim 17 wherein controller receives said electronic image as serial pixel data and determines if said reflection is in said predetermined region before the pixel data for the entire electronic image has been received.

19. The apparatus of claim 18 wherein said electronic image includes a frame comprised of two fields, and wherein said controller determines if said reflection is in said predetermined region in each said field.

20. The apparatus of claim 17 wherein said controller receives said electronic image as serial pixel data indicating image intensity, and wherein said controller includes a comparator that compares the intensity of pixel data at particular pixel positions with a threshold value characteristic of said reflection to determine if said reflection is in said predetermined position.

21. The apparatus of claim 20 wherein said controller includes an occurrence monitor that is connected to said comparator and monitors occurrences of pixel intensity over said threshold.

22. The apparatus of claim 20 wherein said controller includes a line counter that counts lines of pixel data and a pixel counter that counts pixels within a line, and wherein said line counter and said pixel counter enable said comparator to compare intensity values at particular pixel positions.

23. The apparatus of claim 15 further comprising
a position sensor carried on said instrumentation that senses the position of said instrumentation with respect to said eye along a Z axis, and
wherein said controller is responsive to said position sensor to issue a control signal to said apparatus at a predetermined position of said apparatus along said Z axis with respect to said eye.

24. The apparatus of claim 23 further comprising
a motor connected to move said ophthalmic instrumentation along said Z axis with respect to said eye, and
wherein said control signal is a stop motor signal to stop said motor when said instrumentation is at said predetermined position.

25. The apparatus of claim 23 wherein said control signal is said image capture signal, said controller generates said image capture signal upon meeting a Z axis condition and determining the existence of said reflection in a predetermined region within said electronic image.

26. The apparatus of claim 25 wherein said captured image is an image analyzed for a pair of fields that comprise a single video frame while said pair of fields exist.

27. The apparatus of claim 23 wherein said camera includes an array of light sensing elements arranged in rows, and wherein said position sensor includes a source of light that intersects said Z axis and a linear array of optical channels that receive said light from said source, the number of channels receiving light being a function of the position of said instrumentation with respect to said portion of said body, and wherein said optical channels are linked to direct light to a row of said sensing elements in said camera.

28. A patient-aligning ophthalmic apparatus comprising,
a light source that is carried by said ophthalmic apparatus and generates a light beam that is directed along a positioning axis that passes through the center region of a pupil of a patient's eye when said apparatus is aligned with said patient's eye, and
optics causing said light beam to converge in the region to be occupied by a patient's eye and to be imaged on said patient's retina, said light beam being sized so as to fill the majority of a standard pupil size associated with a level of illumination of said apparatus, whereby movement of the center region of the pupil away from said axis will cause said light beam to be eclipsed by said pupil, such that a patient maintaining an uneclipsed view of said beam will be aligned with said axis.

29. The apparatus of claim 28 wherein said light beam is smaller than said standard pupil size by an amount equal to the permitted misalignment of said apparatus.

30. The apparatus of claim 28 wherein said apparatus further comprises
a camera that periodically outputs electronic images of a portion of said patient's eye including the pupil and cornea of said eye,
a controller that receives said electronic images and generates an image capture signal to capture a said electronic image if said electronic image includes a reflection of said beam in a predetermined region within said electronic image, said light beam being smaller than standard pupil size by an amount selected to maintain said reflection within said predetermined region when said image is not eclipsed by the pupil.

31. The apparatus of claim 28 further comprising a target aligned with said axis.

32. An apparatus for determining position of instrumentation with respect to a patient along an axis comprising,
a light source carried by said instrumentation so as to direct a light beam to intersect said axis, and
a linear array of light receiving elements spaced along an optical path from said light source on an opposite side of said axis from said light source so as to provide a region for receiving a portion of said patient between said source and said elements, the number of elements blocked by said portion of said patient being a function of the position of said instrumentation with respect to said patient, and
a detector to detect light received at individual said elements.

33. The apparatus of claim 32 wherein said instrumentation is ophthalmic instrumentation including a tubular member to be positioned at a predetermined distance from said eye along said axis.

34. The apparatus of claim 33 further comprising a motor that moves said instrumentation along said axis and a controller that is responsive to said detector to stop when said instrumentation is located at a desired position with respect to said patient.

35. The apparatus of claim 32 wherein said light receiving elements are optical fibers.

36. The apparatus of claim 35 wherein said optical fibers inked to an array of sensing elements also used to image a portion of said patient.

37. The apparatus of claim 32 further comprising an optical fiber to direct light from source to said region.

* * * * *